United States Patent [19]

Melcher et al.

[11] Patent Number: 4,913,821

[45] Date of Patent: Apr. 3, 1990

[54] METHOD FOR THE DETERMINATION OF PHENOLS IN WATER

[75] Inventors: Richard G. Melcher, Midland, Mich.; Earl E. Burt, III, Cincinnati, Ohio

[73] Assignee: The Dow Chemical Company, Midland, Mich.

[21] Appl. No.: 343,967

[22] Filed: Apr. 27, 1989

[51] Int. Cl.$^4$ .............................................. B01D 15/08
[52] U.S. Cl. .................................... 210/635; 210/656; 210/659; 210/198.2; 210/909; 436/131; 436/140; 436/161; 436/178
[58] Field of Search ............... 436/131, 140, 161, 178; 210/635, 198.2, 259, 321.78, 637, 659, 656, 909; 73/61.1 C

[56] References Cited

U.S. PATENT DOCUMENTS 4,775,476  10/1988  Melcher et al. ...................... 210/635

OTHER PUBLICATIONS

A–*Standard Methods For the Examination of Water and Wastewater*, 574–576, Published by the American Public Health Assoc., American Water Works Assoc. and Water Pollution Control Fed., (14th Ed.), (1976).
B–D. R. Knapp, *Handbook of Analytical Derivatization Reactions*, 29, published by John Wiley & Sons (1979).
C–D. A. Skoog, et al., *Fundamentals of Analytical Chemistry*, 469–471, published by Holt, Rinehart and Winston (1963).
D–Frei, et al., *Chemical Derivatization in Analytical Chemistry, Chromatography* 1m 53–54, published by Plenum Press (1981).
E–P. Jandera, et al., *Gradient Elution in Column Liquid Chromatograph Theory and Practice*, 298, published by Elsevier (1985).

Primary Examiner—Ernest G. Therkorn
Attorney, Agent, or Firm—Timothy S. Stevens

[57] ABSTRACT

A chromatographic method for the determination of individual phenols in water by adding a halogenating agent to the water, e.g., using the bromate-bromide reaction to generate tribromide ions which react with the phenols to form bromo-derivatives of the phenols, then to permeate the bromo-derivatives across a membrane, e.g., a silicone rubber membrane, into a liquid extractant, e.g., a dilute aqueous solution of sodium hydroxide and acetonitrile, and then determining the permeated bromo-derivatives in the liquid extractant by chromatography, e.g., by injecting the liquid extractant containing the permeated bromo-derivatives into a reverse phase liquid chromatographic system. The use of a membrane is essential in the present invention because it allows the use of a high enough concentration of halogenating agent to completely halogenate most any sample and provides for the removal of the halo-derivatives from the halogenation reaction site before any substantial degradation of the halo-derivatives occurs from a relatively high concentration of halogenating agent. Total phenols as a group can be determined by modifying the method to use backflow liquid chromatography to eliminate potential interferences and to elute the halo-derivatives in a single chromatographic peak.

16 Claims, 4 Drawing Sheets

METHOD FOR THE DETERMINATION OF PHENOLS IN WATER

FIELD OF THE INVENTION

The invention is in the field of chemical analysis methods for the determination of phenols in water.

BACKGROUND OF THE INVENTION

The analysis of a water, e.g. waste water or surface water, for phenols is important in determining the quality of the water. The "total phenol" content of the water is often determined by the standard 4-aminoantipyrene colorimetric method as outlined in *Standard Methods For The Examination Of Water And Wastewater*, published jointly by the American Public Health Association, the American Water Works Association and the Water Pollution Control Federation. Individual phenols, such as 2,4,6-trichlorophenol are typically determined by gas or liquid chromatography.

Derivatization is a commonly used sample pretreatment step to enhance the chromatographic characteristics or the detectability of a sample component of interest. For example, many phenols can be derivatized with diazomethane to form a methyl ether of the parent phenol for gas chromatographic analysis and derivatization with 5-dimethylamino-1-naphthaline sulfonyl chloride has been done for fluorescence detection liquid chromatography. *The Handbook of Analytical Derivatization Reactions* authored by Daniel R. Knapp and published by John Wiley & Sons is one source of information regarding derivatization reactions for chromatography.

Phenols have also been titrated by reaction with an excess of bromine produced by the bromate-bromide reaction to brominate the phenol and then a back titration to determine the amount of bromine consumed by the bromination. Different phenols consume different amounts of bromine. For example, phenol, salicylic acid, acetylsalicylic acid, m-cresol, sulfamic acid and m-toluidine consume three moles of $Br_2$ per mole of the phenol (to produce a tribrominated moiety) while beta-naphthol consumes only one mole of $Br_2$. More information on the titration of phenols with bromine can be had by reference to *Fundamentals of Analytical Chemistry* authored by Skoog and West and published by Holt, Rinehart and Winston. Phenols are not generally bromination titrated in samples of surface water because in such water the concentration of phenols is almost always below the reliable detection limit of the method.

Backflow liquid chromatography is a known technique wherein a sample is injected into the inlet end of a liquid chromatographic column and developed by a flow of the liquid mobile phase directed into the inlet end of the column until the earliest to elute component of interest of the sample is just about to elute from the outlet end of the column. Then, the flow of mobile phase is reversed through the column so that the sample components in the column "roll up" toward the inlet end of the column and tend to elute from the inlet end of the column as a single chromatographic band. By this technique, sample components that elute from the outlet end of the column before the earliest to elute component of interest nears the outlet end of the column are discarded and do not become part of the single chromatographic band mentioned above.

Membrane assisted chromatography is a known technique wherein a membrane is used to partition a sample containing a component of interest from an extractant. The component of interest permeates across the membrane into the extractant which is then subjected to a chromatographic determination. The specific membrane and extractant used are selected to enhance the permeation of the sample component of interest and to minimize or eliminate the permeation of other components of the sample that may interfere with the chromatographic determination of the component of interest. U.S. Pat. No. 4,775,476 to Richard G. Melcher and Hernan J. Cortes is an example of membrane assisted liquid chromatography.

The "total phenol" 4-aminoantipyrene colorimetric method does not determine individual phenols. However, it can be important to determine the individual phenols that make up the "total phenols" and it should be noted that not all phenols respond or respond equally in the 4-aminoantipyerene colorimetric method. High Performance Liquid Chromatography (HPLC) with an ultraviolet detector or an electrochemical detector can be used to determine the individual phenols but several problems can occur. First, the different phenols, e.g., phenol and 2,4,6-trichlorophenol, can have different spectrophotometric molar absorptivities at the detection wavelength, different maximum absorption wavelengths and, for the electrochemical detector, different electrochemical reaction characteristics. Second, the different phenols, e.g., phenol and 2,4,6-trichlorophenol, can have significantly different chromatographic characteristics. In reverse phase HPLC, phenol tends to elute early in the chromatogram with other interfering non-phenol components of the sample.

Frei et al., *Chemical Derivatization in Analytical Chemistry, Chromatography*, 1, 53–54, (1981), published by Plenum Press, pointed to a possible solution to these problems, i.e., treat a sample of water with bromine to brominate any phenols in the water, extract the brominated phenols from the water and then chromatograph the extracted brominated phenols. Jandera et al., *Gradient Elution In Column Liquid Chromatography Theory And Practice*, 298, (1985), published by Elsevier, suggests that halogenated phenols tend to elute later in a reverse phase chromatogram than their parent non-halogenated phenols and many liquid chromatographers know this as general knowledge from experience. However, when the present inventors tried the approach pointed to in Frei et al., it was discovered that the brominated phenols were apparently being partially destroyed by the remaining bromine during the bromination process, probably by a mechanism analogous to superchlorination. This destruction problem could be controlled by reducing the bromine concentration during the bromination step and by reducing the time of the bromination step but then the procedure was not applicable for samples that contained enough phenols and other components to substantially use up all of the bromine added during the bromination step before all of the phenols were completely brominated. A bromination derivatization chromatographic method is needed for the determination of phenols in water that solves this problem.

SUMMARY OF THE INVENTION

The present invention is a chromatographic method for the determination of phenols in water wherein the phenols are derivatized with a halogenating agent to produce halogenated phenols that have more similar detection characteristics and more similar chromatographic characteristics relative to the parent unhalogenated phenols originally in the water and which solves to a substantial degree the above mentioned problem as soon will be revealed. The present invention has one embodiment for the determination of one or more phenols each with their own chromatographic response and another embodiment for the determination of total phenols as a single liquid chromatographic response.

The embodiment for the determination of one or more phenols each with their own chromatographic response comprises four steps. The first step is to introduce a halogenating agent into the water such as by adding bromine directly to the water or by using the bromate-bromide reaction to generate tribromide ion in the water. The second step is to react the halogenating agent with the phenol to form a halo-derivative of the phenol. The third step is to permeate the halo-derivative of the phenol across a membrane, such as a silicone rubber membrane, into a liquid extractant, such as a dilute aqueous solution of sodium hydroxide and acetonitrile. This step is at the heart of the invention and apparently separates the halo-derivative of the phenol from the halogenating agent added to the water before the halogenating agent can substantially destroy the halo-derivative of the phenol and allows the use of enough of halogenating agent to halogenate most any water. The last step is to determine the halo-derivative of the phenol by chromatography, such as reverse phase liquid chromatography or gas chromatography.

The embodiment for the determination of total phenols as a single liquid chromatographic response also comprises four steps, the first three of which are almost the same as above. The first step is to introduce a halogenating agent into the water such as by adding bromine directly to the water or by using the bromate-bromide reaction to generate tribromide ion in the water. The second step is to react the halogenating agent with the phenols to form halo-derivatives of the phenols in the water. The third step is to permeate the halo-derivatives of the phenols across a membrane into a liquid extractant. The last step is to determine the halo-derivatives of the phenols in the receiving liquid by backflow liquid chromatography. The use of the backflow technique in this step places substantially all of the phenol derivatives in a single peak and discards many interfering components.

DETAILED DESCRIPTION OF THE INVENTION

Figure 1:
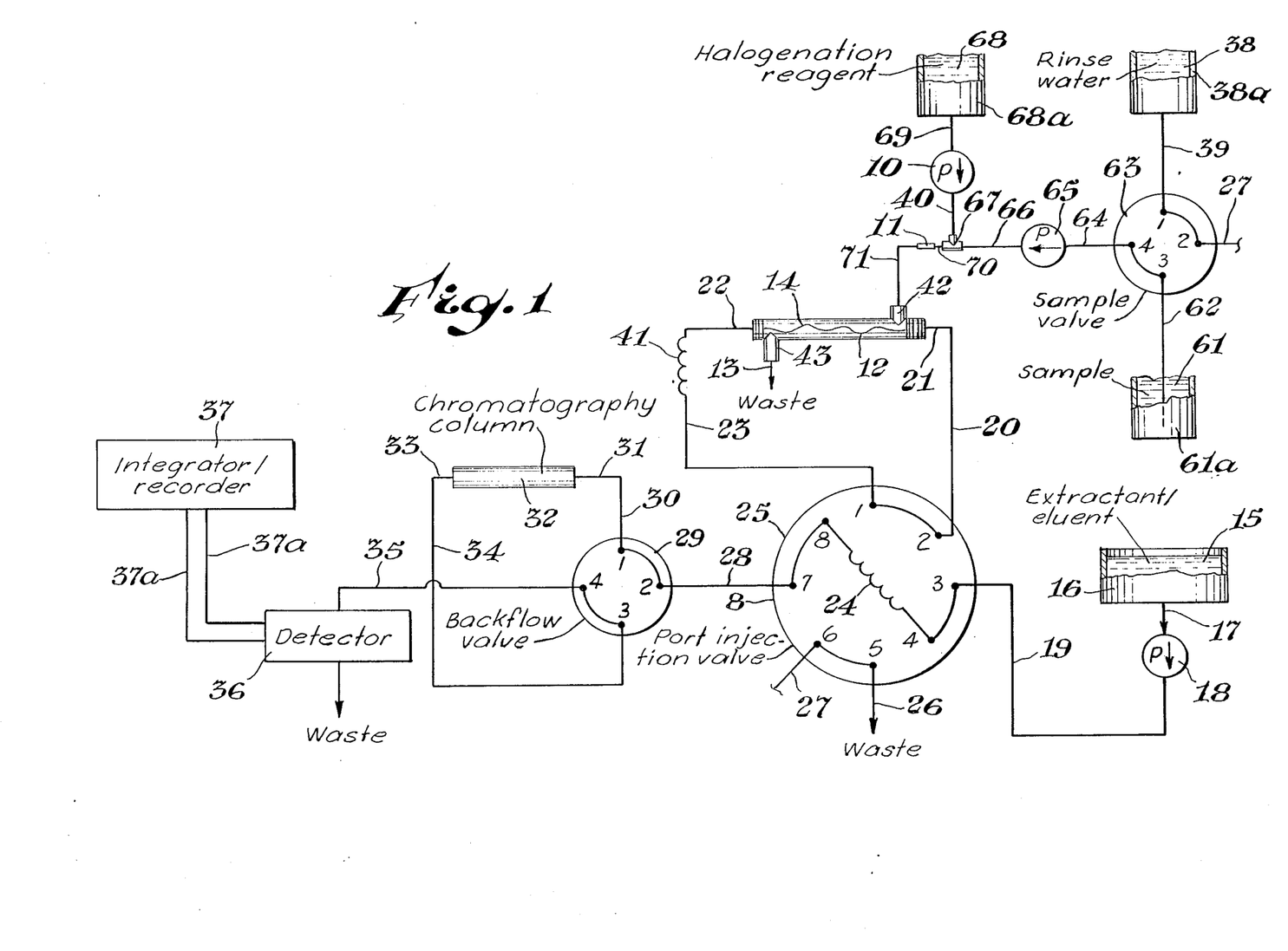
FIG. 1 is a schematic drawing of an apparatus used to perform the method of the present invention including an injection valve, a sample valve and a backflow valve, each of which are two position valves shown in one position.
Figure 2:
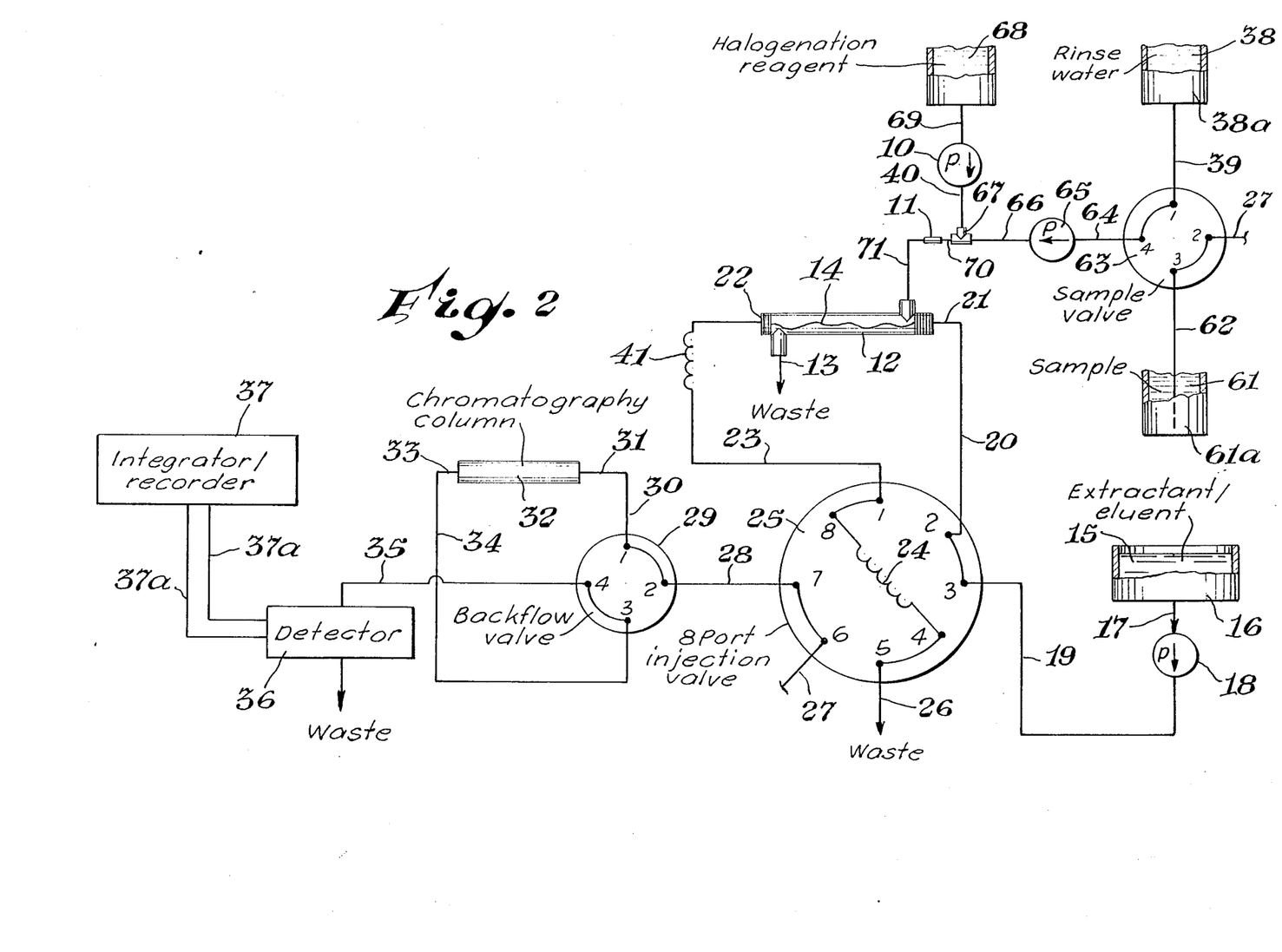
FIG. 2 is a schematic drawing of the apparatus shown in FIG. 1 with the sample valve and the injection valve shown in the other position.
Figure 3:
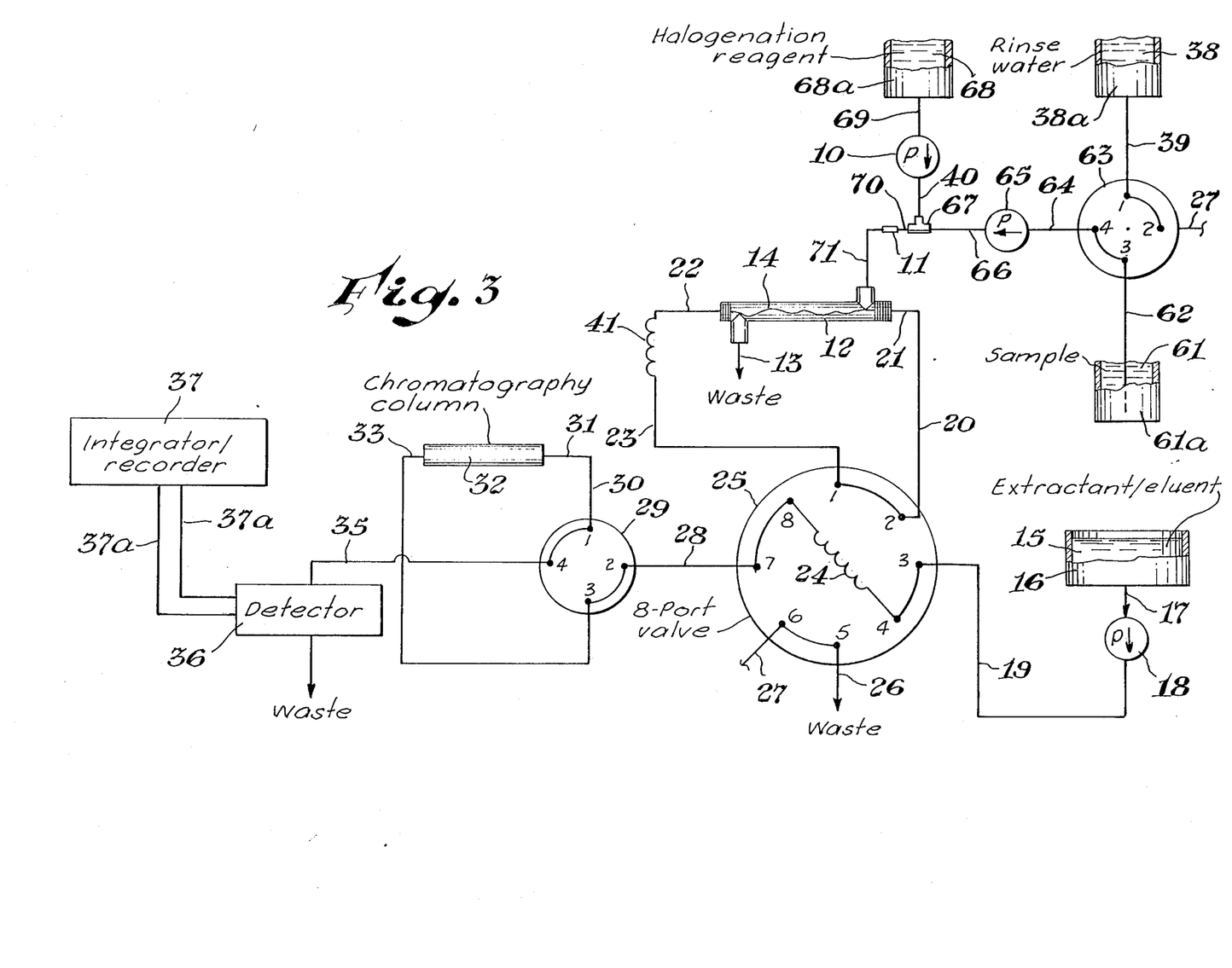
FIG. 3 is a schematic drawing of the apparatus shown in FIG. 1 with the backflow valve shown in the other position; and, FIG. 4 is a front view, mostly in full and partly broken away and in section, showing a preferred membrane cell for use with the present invention.

Referring now to FIGS. 1, 2 and 3, therein is shown a schematic drawing of one apparatus that can be used to perform the method of the present invention, including a two-position 8-port injection valve 25 (such as a C8UW- valve from Valco Instrument Co., Houston, Tex.) shown in one position in FIG. 1 and in the other position in FIG. 2. A reservoir 16 is provided for containing a liquid extractant/eluent 15. A length of tubing 17 connects the reservoir 16 with a liquid chromatography pump 18 (such as an M-45 pump from Waters Associates, Milford, Mass.). The pump 18 is connected to port 3 of the valve 25 by a length of tubing 19 (1/16 stainless steel tubing and fittings are used generally herein to conduct the extractant/eluent 15 and are available from The Anspec Co., Ann Arbor, Mich.). A sample loop 24 is connected to ports 4 and 8 of the valve 25. As shown in FIG. 1, the ports 1 and 2, 3 and 4, 5 and 6, and 7 and 8 of the valve 25 are internally connected. Port 6 of the valve 25 is closed off by a plug 27. A waste line 26 is connected to port 5 of the valve 25. A length of tubing 28 is used to connect port 7 of the valve 25 with port 2 of a two position 4-port backflow valve 29 (such as a C4UW valve from Valco, supra) shown in one position in FIG. 1 and in the other position in FIG. 3. As shown in FIG. 1, the ports 1 and 2, and 3 and 4 of the valve 29 are internally connected. Port 1 of the valve 29 is connected to the inlet 31 of a chromatography column 32 (such as a 4.6×30 millimeter Brownlee PRP-1 polymeric guard column available as catalog No. H1502 from Anspec, supra). The outlet 33 of the column 32 is connected to port 3 of the valve 29 by a length of tubing 34. Port 4 of the valve 29 is connected to a liquid chromatography detector 36 (such as a Kratos Spectroflow 773 variable wavelength detector) by a length of tubing 35. An integrator/recorder 37 (such as a Spectraphysics 4270 integrator/recorder) is electrically connected to the detector 36 by the wires 37a.

A sample reservoir 61a contains sample 61. The reservoir 61a is connected to port 3 of a two position 4-port valve 63 (such as a C4UW valve from Valco, supra) shown in one position in FIG. 1 and in the other position in FIG. 2 by a length of tubing 62. As shown in FIG. 1, the ports 1 and 2, and 3 and 4 of the valve 63 are internally connected. Port 2 of the valve 63 is closed off by a plug 27. A rinse water reservoir 38a contains rinse water 38 (such as distilled water). The reservoir 38a is connected to port 1 of the valve 63 by a length of tubing 39. Port 4 of the valve 63 is connected to a pump 65 (such as a FMI Jr. Lab Pump, Anspec, supra) by a length of tubing 64. A reagent reservoir 68a contains a halogenation reagent 68 (such as 0.03 molar tribromide ion in 2 molar hydrochloric acid). The reservoir 68a is connected to a pump 10 (such as a FMI Jr. Lab Pump, Anspec, supra) by a length of tubing 69. The pump 10 is connected to a tee 67 by a length of tubing 40. The pump 65 is connected to the tee 67 by a length of tubing 66 (1/16 inch o.d., 1/32 inch i.d. tubing, made from Teflon brand polymer and associated fittings available from Anspec, supra, are used generally herein to conduct the sample 61, the rinse water 38 and the halogenation reagent 68). The tee 67 is connected to an in-line mixer 11 (such as a three millimeter diameter tube that is thirty millimeters long and packed with coarse glass chips) by a length of tubing 70. The in-line mixer 11 is connected to the shell side inlet 42 of a membrane cell 12 by a length of tubing 71. A length of tubing 13 is directed from the shell side outlet 43 of the cell 12 to waste. The tube side inlet 21 of the cell 12 is connected to port 2 of the valve 25 by a length of tubing 20. The tube side outlet 22 of the cell 12 is connected to a delay coil 41 (such as one hundred centimeters of the Teflon tubing). The delay coil 41 is connected to port 1 of the valve 25 by a length of tubing 23.

Figure 4:
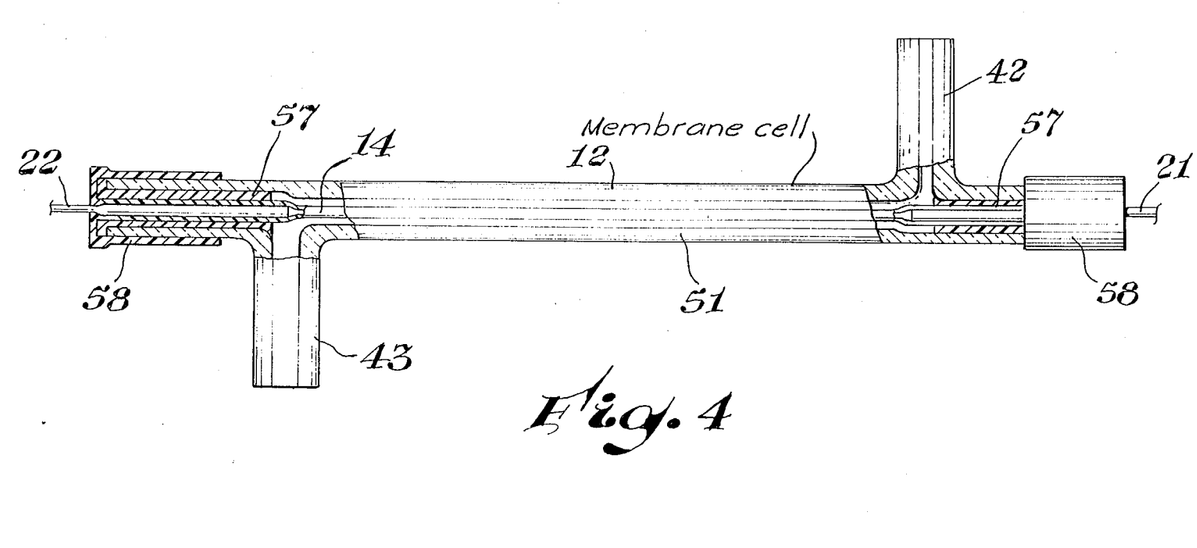

FIG. 4 shows the membrane cell 12 in greater detail. The membrane cell 12 has a three hundred millimeter long, two millimeter internal diameter glass shell 51 provided with a shell side inlet 42 and a shell side outlet 43. The tube side inlet 21 and the tube side outlet 22 consist of 1/32 outside diameter tubing made from Teflon brand polymer. A tubular silicone rubber membrane 14 (such as Dow Corning Silastic brand medical tubing, twelve thousands of an inch internal diameter and twenty thousands of an inch outside diameter) is connected to the inlet tubing 21 and the outlet tubing 22 by first placing the membrane 14 ends into xylene to swell the membrane ends. The swollen membrane ends are then slipped over the inlet tubing 21 and the outlet tubing 22 and sealed into the shell 51 using Dow Corning RTV Silicone Rubber Sealant 57. Installation of plastic caps 58 completes the cell 12.

The chemical analysis chromatography method for the determination of a phenol in a water will now be discussed with reference to FIGS. 1 and 2. At the start of the analysis cycle, the valves 25, 29 and 63 are in the position shown in FIG. 1. The extractant/eluent 15 is pumped by the pump 18 through the valve 25, the valve 29, the column 32 and the detector 36 to waste. The sample 61 is water containing at least one phenol dispersed in it and is pumped by the pump 65 to the tee 67. Simultaneously, the pump 10 pumps the halogenation reagent 68 to the tee 67 to introduce the halogenation reagent 68 into the flowing stream of sample 61. The combined streams then flow through the in-line mixer 11, where more through mixing of the two streams occurs which promotes a more complete halogenation reaction between the halogenation reagent and the phenol of the sample to form a halo-derivative of the phenol. The combined streams then flow into the membrane cell 12 contacting the outside of the tubular membrane 14. The extractant/eluent 15 occupies the inside of the tubular membrane 14. At least a portion of the halo-derivative of the phenol permeates across the membrane 14 into the extractant/eluent 15 inside the membrane 14. After a defined period of time, the valve 25 and the valve 63 are rotated to their other position as shown in FIG. 2 and the pump 10 is turned off. The pump 65 flows the rinse water 38 through the cell 12 and the extractant/eluent 15 inside the membrane 14 is then flowed through the delay coil 41, and into the sample loop 24. Then, the valve 25 is again switched to the position shown in FIG. 1 so that the contents of the loop 24 are flowed through the valve 29, the column 32 and the detector 36 to obtain a chromatogram of the halo-derivative of the phenol as generated by the integrator/recorder 37 and to determine the halo-derivative of the phenol in the extractant/eluent by liquid chromatography. Another analysis cycle is begun when the pump 10 is turned on and the valve 63 is rotated to the position shown in FIG. 1.

The delay coil 41 is generally needed to increase the length of time that the extractant/eluent 15 is flowed through the membrane 14 to substantially flush and desorb all of the halo-derivative of the phenol from the cell 12 before the main portion of the permeated halo-derivative of the phenol in the extractant/eluent 15 is flowed into the loop 24 as shown in FIG. 2. However, the coil 41 is not critical and if not used, then the valve 25 can be temporarily rotated to the position shown in FIG. 2 after the chromatogram is generated to flush out the cell 12 before beginning another analysis cycle. The timing of the rotation of the valve 25 from the position shown in FIG. 1 to the position shown in FIG. 2 can be determined by temporarily connecting the detector 36 to port 5 of the valve 25 to determine when the main portion of the permeated halo-derivative of the phenol in the extractant/eluent 15 is flowed into the loop 24 as shown in FIG. 2. However, the flow through cell of the detector 36 may need to be modified for this determination to reduce its back pressure to keep from bursting the membrane 14, e.g., by temporarily replacing any fine capillary tubing of the flow cell with larger diameter tubing.

If the sample 61 contains at least two phenols and if after the valve 25 is rotated to the position shown in FIG. 2, the valve 29 is rotated to the position shown in FIG. 3, then backflow liquid chromatography can be accomplished to determine total phenols in the sample 61 as described in Example 2, below.

The specific extractant liquid used in the present invention is not critical as long as at least a detectable portion of the halo-derivative of the phenol permeates across the membrane into the extractant. Preferably, for the sake of simplicity, the extractant has the same composition as the eluent as taught by Melcher and Cortes in U.S. Pat. No. 4,775,476, supra. However, if the chromatography used is gas chromatography, then this is not possible. Example 3 below describes the use of gas chromatography in the present invention.

The specific halogenating agent used in the present invention is not critical as long as it halogenates most phenols in water. Such halogenating agents are well known and include $Cl_2$. The preferred halogenating agent is a brominating agent which supplies $Br_2$, $Br_3^-$ or other form of reactive bromine for the bromination of phenolic compounds. A preferred brominating agent is $Br_3^-$ prepared by dissolving 10.0 grams of potassium bromide and 1.67 grams of potassium bromate in one liter of water and then taking ten milliliters of this solution to one liter with 2 normal hydrochloric acid. The bromate, bromide and acid react to form bromine and water (the bromate-bromide reaction). The excess bromide in the above recipe reacts with the bromine to form the tribromide ion $Br_3^-$. Alternative brominating reagents that are contemplated to work in the present invention include but are not limited to bromine water and aqueous solutions containing dibromonitrilopropionamide (an organic based brominating agent).

The specific membrane used in the present invention is not critical but a silicone rubber membrane is preferred. The membrane can be flat in shape and form a portion of a channel cut, for example, in a stainless steel or Teflon block. The membrane can be tubular in shape and the tube can be relatively small in diameter, e.g., 0.025 inches or smaller or larger. The membrane should not, however, be of the porous type when the liquid extractant is miscible with water or if a porous type membrane is used in this instance, then its pores should be filled so that there are no open pores through the membrane for normal fluid flow, i.e., the halo-derivative of the phenol is believed to dissolve into the membrane from the mixture of the halogenation reagent and the water and then desorbed from the other side of the membrane by the extractant liquid. If the liquid extractant is not miscible with water (as in Example 3 below), then a porous membrane (such as Celgard brand porous polypropylene membrane from the Celanese Corp.) can be used. The use of a membrane is critical in the present invention because the membrane allows the use of a halogenation reagent having a sufficiently high concentration of halogenating agent to completely halogenate most samples but apparently facilitates removal of the halo-derivative of the phenol before the excess halogenating agent substantially destroys the halo-derivative of the phenol. An additional benefit of the use of a membrane in the present invention, of course, is the selectivity it can provide when interfering components (including solids in a sample) do not permeate across the membrane.

EXAMPLE 1

The system of FIG. 1–4 as described above is assembled. Each valve in the system is equipped with an air actuator for automatic operation. The detector is set at 300 nanometers. The integrator/recorder contains an external event module which turns the pumps on and off and rotates the air actuated valves on command from a predetermined program as is well understood in the art. The extractant eluent is 18 percent acetonitrile and 82 percent 0.01 molar sodium hydroxide pumped at a flow rate of 400 microliters per minute. The rinse water is made basic by adding 10 milliliters of 1N sodium hydroxide per liter (which speeds rinsing of the membrane cell). The sample loop contains a fixed volume of 16 microliters. The delay coil has a fixed volume of approximately 150 microliters. The sample contains 1 part per million (ppm) each of phenol, 4-chlorophenol, 2,4-dichlorophenol, 2,4,6-trichlorophenol, and 2,3,4,6-tetrachlorophenol in water. The sample is pumped at a flow rate of 1 milliliter per minute. The halogenation reagent is the $Br_3^-$ bromination reagent, supra, and is pumped at a flow rate of 1 milliliter per minute. After 10 minutes of operation as shown in FIG. 1, the reagent pump is turned off and the sample valve is rotated to the position shown in FIG. 2. After an additional 3 minutes of operation, the injection valve is rotated to the position shown in FIG. 2 for 0.45 minutes. Then the injection valve is rotated back to the position shown in FIG. 1 to inject the contents of the sample loop onto the chromatography column. The integrator/recorder traces a chromatogram over the next 17 minutes (during which time another sample can be derivatized and permeated). The chromatogram shows a peak at 2.9 minutes for 2,4,6-trichlorophenol (which does not brominate under these conditions), a peak at 3.3 minutes for 2,4-dichlorophenol (which has been brominated to the halo-derivative 2-bromo-4,6-dichlorophenol, a peak at 4.0 minutes for 4-chlorophenol (which has been brominated to the halo-derivative 2,6-dibromo-4-chlorophenol, a peak at 5.3 minutes for phenol (which has been brominated to the bromo-derivative 2,4,6 -tribromophenol) and a peak at 9.0 minutes for 2,3,4,6-tetrachlorophenol (which does not brominate under these conditions). If the same sample is run without the bromination reagent flowing, then only the 2,4,6-trichlorophenol and 2,3,4,6-tetrachlorophenol peaks are observed which can be used as an additional confirmation of peak identity. The system is used to determine phenol in water over the range of from 10 parts per billion (ppb) to 10 ppm. The upper range can be extended by increasing the brominating agent concentration in the bromination reagent, by slowing the flow rate of the sample pump, and by increasing the flow rate of the reagent pump. This example teaches a preferred aspect of the present invention for the determination of individual phenols in a water sample using liquid chromatography.

EXAMPLE 2

The system of Example 1 is used in this example for the determination of total phenols. The backflow valve is rotated to the position shown in FIG. 3 two and one half minutes after the injection valve injects the permeated bromo-derivatives onto the column. At this point the phenols and bromo-derivatives of the phenols are still in the chromatography column but many interferences have already eluted from the column, and when the backflow valve is rotated to the position shown in FIG. 3, then the phenols and bromo-derivatives of the phenols are back eluted from the column substantially as one chromatographic band to be detected by the detector and recorded as a single peak eluting at 5 minutes. Although this procedure may show some response for compounds other than phenols, it is made highly selective for phenols by using an extractant/eluent that is relatively low in organic modifier (18% acetonitrile) and is basic (0.01 N sodium hydroxide) so that the phenolic compounds form phenate salts which concentrate in the extractant/eluent and are not re-absorbed by the membrane. In addition, the detector wavelength is set at 300 nanometers which is the region of high spectrophotometric absorptivity of brominated and chlorinated phenols and low absorptivity of many other components which may permeate the membrane. This example teaches a preferred aspect of the present invention for the determination of total phenols in a water sample using backflow liquid chromatography.

EXAMPLE 3

The system of Example 1 is used with modification in this example for the determination of individual phenols in a water sample using gas chromatography. This is accomplished, among other things, by not using the backflow valve 29 and by changing the injection valve 25 to a pair of air actuated two position 4-port Valco valves (a C4UW selection valve and a A214UPW1 internal slot injection valve) so that in one position of the selection valve the extractant by passes the cell 12 and flows directly to the injection valve and in the other position the extractant flows through the membrane 14 and then to the injection valve. The injection valve has a one microliter volume internal slot and is mounted on a Hewlett Packard 890 gas chromatograph having an electron capture detector. The column used is a 15 meter long J&W Scientific fused silica capillary column having an internal diameter of 0.53 millimeter and a DB-5 stationary phase 1.5 micrometers thick. The carrier gas is helium at a carrier gas flow rate of about 5 milliliters per minute. At the detector, nitrogen makeup gas at a flow rate of about 30 milliliters per minute is used. A Nelson Analytical Model 3000 Chromatography Data System is used for the integrator/recorder 37 and for automatically switching the valves. The oven of the gas chromatograph is programmed to be 40° C. for three minutes after injection and then to rise at a rate of 15° C. per minute to a temperature of 100° C., and then at a rate of 6° C. per minute to a temperature of 220° C. The extractant is hexane pumped at a flow rate of 100 microliters per minute. The membrane 14 is changed to a tubular silicone rubber membrane having an internal diameter of 0.02 inches and an external diameter of 0.037 inches connected to inlet and outlet tubing 21 and 22 of 1/16 inch stainless steel tubing. The silicone rubber membrane swells and lengthens when exposed to the hexane and the inlet and outlet tubing 21 and 22 is positioned to adjust the length of the membrane. The sample contains 1 ppb of phenol and when the injection valve is rotated to inject the permeated and extracted 2,4,6-tribromophenol derivative of phenol, the helium carrier gas pressure is simultaneously increased to 20 psig for two seconds to reduce injection valve carry-over. At 16 minutes the data system records a peak for 2,4,6-tribromophenol. If the bromination reagent is not used, no peak is observed for phenol. The hexane extractant is not selective for phenols and will extract many other components from the sample, however, the resolution of the capillary gas chromatograph column is high enough to separate many components. In addition, the electron capture detector is highly responsive to compounds containing bromine and has a relatively low response to many other components which may be permeated across the membrane into the extractant. This example teaches a preferred aspect of the present invention for the determination of individual phenols in a water sample using gas chromatography.

What is claimed is:

1. A chemical analysis chromatography method for the determination of a phenol in a water, comprising the steps of:
    (a) introducing a halogenating agent into the water;
    (b) reacting the halogenating agent with the phenol to form a halo-derivative of the phenol;
    (c) permeating the halo-derivative of the phenol across a membrane into a liquid extractant; and
    (d) determining the halo-derivative of the phenol in the liquid extractant by chromatography.

2. The method of claim 1 wherein in step (d) the halo-derivative is determined by liquid chromatography.

3. The method of claim 2 wherein the halogenating agent is a brominating agent and the halo-derivative is a bromo-derivative.

4. The method of claim 3 wherein the brominating agent comprises tribromide ion.

5. The method of claim 3 wherein the membrane is a silicone rubber membrane.

6. The method of claim 1 wherein in step (d) the halo-derivative is determined by gas chromatography.

7. The method of claim 6 wherein the halogenating agent is a brominating agent and the halo-derivative is a bromo-derivative.

8. The method of claim 7 wherein the brominating agent comprises tribromide ion.

9. The method of claim 7 wherein the membrane is a silicone rubber membrane.

10. The method of claim 1 wherein the halogenating agent is a brominating agent and the halo-derivative is a bromo-derivative.

11. The method of claim 10 wherein the brominating agent comprises tribromide ion.

12. The method of claim 10 wherein the membrane is a silicone rubber membrane.

13. A chemical analysis liquid chromatography method for the determination of total phenols in a water, comprising the steps of:
    (a) introducing a halogenating agent into the water;
    (b) reacting the halogenating agent with the phenols to form halo-derivatives of the phenols;
    (c) permeating the halo-derivatives of the phenols across a membrane into a liquid extractant; and
    (d) determining the halo-derivatives of the phenols in the liquid extractant by backflow liquid chromatography.

14. The method of claim 13 wherein the halogenating agent is a brominating agent and the halo-derivative is a bromo-derivative.

15. The method of claim 14 wherein the membrane is a silicone rubber membrane.

16. The method of claim 13 wherein the brominating agent comprises tribromide ion.

* * * * *

UNITED STATES PATENT AND TRADEMARK OFFICE
CERTIFICATE OF CORRECTION

PATENT NO. : 4,913,821

DATED : April 3, 1990

INVENTOR(S) : Richard G. Melcher and Earl E. Burt III

It is certified that error appears in the above-identified patent and that said Letters Patent is hereby corrected as shown below:

Column 8, line 43 "by passes" should correctly read --by-passes--.

Column 8, line 53 "a carrier" should correctly read --a column head pressure of about 10 psig which results in a carrier--.

Signed and Sealed this

Eleventh Day of August, 1992

Attest:

DOUGLAS B. COMER

*Attesting Officer*   *Acting Commissioner of Patents and Trademarks*